US005720734A

United States Patent [19]

Copenhaver et al.

[11] Patent Number: 5,720,734

[45] Date of Patent: Feb. 24, 1998

[54] GASTROSTOMY FEEDING PORTS

[75] Inventors: Rebecca Copenhaver, Mooresville; Mark DeLegge, Davidson, both of N.C.; Ronald D. Russo, Barrington, R.I.

[73] Assignee: Wilson-Cook Medical, Inc., Winston-Salem, N.C.

[21] Appl. No.: 701,430

[22] Filed: Aug. 22, 1996

Related U.S. Application Data

[63] Continuation-in-part of Ser. No. 441,054, May 15, 1995, which is a continuation-in-part of Ser. No. 202,443, Feb. 28, 1994.

[51] Int. Cl.[6] .......... A61M 5/00

[52] U.S. Cl. .......... 604/247; 604/27; 604/48; 604/256

[58] Field of Search .......... 604/247, 96, 27, 604/48, 277, 332, 256, 175

[56] References Cited

U.S. PATENT DOCUMENTS

| | | |
|---|---|---|
| 3,915,171 | 10/1975 | Shermeta . |
| 4,315,513 | 2/1982 | Nawash et al. . |
| 4,356,391 | 10/1982 | Stewart . |
| 4,393,873 | 7/1983 | Nawash et al. . |
| 4,685,901 | 8/1987 | Parks . |
| 4,717,385 | 1/1988 | Cameron et al. . |
| 4,808,162 | 2/1989 | Oliver . |
| 4,834,712 | 5/1989 | Quinn et al. . |
| 4,863,438 | 9/1989 | Gauderer et al. . |
| 4,900,306 | 2/1990 | Quinn et al. . |
| 4,944,732 | 7/1990 | Russo . |
| 5,007,900 | 4/1991 | Picha et al. . |
| 5,073,166 | 12/1991 | Parks et al. . |
| 5,080,650 | 1/1992 | Hirsch et al. . |
| 5,112,310 | 5/1992 | Grobe . |
| 5,125,897 | 6/1992 | Quinn et al. . |
| 5,251,873 | 10/1993 | Atkinson et al. . |
| 5,255,676 | 10/1993 | Russo . |
| 5,336,203 | 8/1994 | Goldhardt et al. . |
| 5,342,321 | 8/1994 | Potter . |
| 5,360,417 | 11/1994 | Gravener et al. . |
| 5,402,982 | 4/1995 | Atkinson et al. . |
| 5,411,491 | 5/1995 | Goldhardt et al. . |
| 5,413,565 | 5/1995 | Michels et al. . |
| 5,501,426 | 3/1996 | Atkinson et al. . |

OTHER PUBLICATIONS

"Announcing The Gauderer Genie System", Bard Interventional Products Division, C.R. Bard, Inc.

*Primary Examiner*—Michael Powell Buiz
*Assistant Examiner*—N. Kent Gring
*Attorney, Agent, or Firm*—Woodard, Emhardt, Naughton Moriarty & McNett

[57] ABSTRACT

Gastrostomy ports are disclosed for reliably providing enteral feeding to a patient over long periods of time. Gastrostomy ports shown herein provide one-way valves which include a resilient valve member which is compressively fitted within a receiving cavity defined by a rigid compression collar. The valve member has a diaphragm portion defining a slit. The compression collar presses inwardly against the outer peripheral edge of the diaphragm portion to apply laterally compressive forces which bias the slit toward a normally closed position. Gastrostomy ports are further shown for accessing the interior of a body cavity or organ which are self retaining and resist inadvertent pull-out but can be atraumatically implanted and removed. The devices include a retaining element which is resiliently deformable between a normally enlarged state for retention and a collapsed state for insertion and removal through a stoma and are provided with means for controllably biasing the element toward a longitudinal axis for collapsing the element. Still additional embodiments are disclosed which provide for the direct conversion of an implanted PEG tube into a low profile feeding port, and which further provide for the direct secure connection to an enteral feeding tube adapter.

13 Claims, 11 Drawing Sheets

GASTROSTOMY FEEDING PORTS

This is a continuation-in-part of application Ser. No. 08/441,054 filed on May 15, 1995, now pending which is a continuation-in-part of application Ser. No. 08/202,443 filed on Feb. 28, 1994 now pending.

FIELD OF THE INVENTION

This invention broadly relates to medical devices, and particularly relates to gastrostomy feeding ports.

BACKGROUND OF THE INVENTION

Gastrostomy feeding ports provide access to the stomach at a stoma site. Such ports are typically left in place over a prolonged period of time and are used for feeding and medicating the patient over this period. Gastrostomy feeding ports are usually low profile, fitting fairly flush to the skin surface to minimize patient discomfort, improve aesthetics and help to prevent unnecessary irritation to the stomal area. In the design of a long term implanted device such as a gastrostomy port several factors must be considered, such as biocompatibility and patient comfort as well as enhanced function of the device.

One problem with gastrostomy ports in particular is that the link they provide between the stomach and the exterior of the body creates a potential for leakage of gastric contents. This leakage or reflux of gastric contents is particularly troublesome because the highly acidic materials can cause severe skin burns or tissue maceration leading to chronic skin infections. This is complicated by the requirement that the port be used repeatedly over a long period of time which increases the potential for leakage. This requirement that a gastrostomy port prevent reflux while allowing convenient and repeated access to the stomach has presented a difficult design problem.

To address the need to prevent reflux while allowing convenient access through the device to the stomach, some gastrostomy ports include check valves. U.S. Pat. No. 4,944,732 discloses a device, commercially available as the Gastro-Port from Sandoz Nutrition Corp., that includes an anti-reflux valve located outside the body in a removable screw cap. Since the valve portion is removable it can be repaired or replaced as needed without replacing the entire feeding port. The Button Replacement Gastrostomy Device is another commercially available gastrostomy feeding port which includes an anti-reflux valve. In the Button device, the anti-reflux valve is located in the distal tip of the device inside the stomach.

As a long term indwelling catheter, a gastrostomy feeding port requires a positive seal for many repeated uses over a long period of time. Unfortunately, some of the prior art gastrostomy feeding port valves have failed to prevent reflux, particularly after many repeated uses. Consequently, some gastrostomy feeding ports, such as the Button and Gastro-Port devices, are supplied with closure caps which positively seal the port entrance while the port is not being used. Closure caps, however, are inconvenient because they must be removed prior to each use of the port and reapplied onto the port after each such use. Over the course of time that a single port is left in place, the cap must be removed and replaced hundreds of times. Should the cap be forgotten or not properly closed about the port even a single time, unintended leakage may consequently occur.

There is a need for a long term indwelling gastrostomy feeding port, with an entrance valve that provides a positive sealing effect over the course of many recurrent uses of the valve and over an extended period of time. Such a device would eliminate the need for a closure cap and would be both safer and more convenient to use than devices that have been provided in the past.

Prior to the implantation of a low profile gastrostomy port, it is common to implant a long, smooth walled Percutaneous Endoscopic Gastrostomy (PEG) tube for enteral feeding or medication. After a time, the PEG tube is removed and replaced with a low profile device, which is more convenient to the patient, especially when a bedstricken patient becomes able to resume a more mobile lifestyle. It is common to remove the PEG tube in its entirety and replace the PEG with a low profile device in the stoma site where the PEG tube had been. While it would be desirable to reduce the trauma and increased risk of infection resulting from completely removing the PEG tube by, instead, directly converting the PEG tube that has already been placed into a low profile device, the converting port device must securely and reliably attach to the PEG tube so that the connection does not loosen over the length of time that the port is left in place. Accordingly, there is a need for a device which directly converts a long PEG feeding tube into a reliable low profile gastostomy feeding port. The conversion should be easy to accomplish and provide for the reliably secure connection of the valve mechanism to the implanted PEG tube.

There is a further need to provide a gastrostomy port device which provides for the securely sealed direct connection to a standard enteral feeding adapter. Such a port would be more convenient as it would remove the need to use intermediate tubing connections.

Gastrostomy ports should also be reliably self-retaining over the long period of time that they may be left in place on a patient. For this purpose, gastrostomy ports commonly include an enlarged retaining structure for placement within the stomach to keep the port in its desired location. The retaining structure contacts the internal surface of the stomach wall surrounding the stomal opening to resist inadvertent pull-out of the device.

To reduce the trauma of insertion into and removal from a stomal site, some devices have included inflatable/deflatable balloon elements which can be inflated through an inflation lumen as disclosed in U.S. Pat. Nos. 5,342,321 to Potter and 5,125,897 to Quinn et al. Other references disclose restraining an enlarged deformable element with pressure on the external surface of the element to collapse the element. U.S. Pat. No. 4,315,513 to Nawash et al. discloses a deformable retaining element which is elongated and compressed into a biodegradable material which will dissolve in the stomach thus allowing expansion of the retaining element. Using a similar approach, Michels et al. discloses inserting a port having a deformable retaining element with a trocar. The retaining element can be collapsed within a semi-rigid casing and inserted into the trocar for placement through the stoma. The casing is removed from the element to allow expansion once it is inserted within the stomach.

Other references disclose deforming a retaining element by insertion of an obturator or similar device. For example, U.S. Pat. Nos. 4,863,438 to Gauderer et al. and 4,944,732 to Russo disclose an enlarged retaining element which is deformable to a collapsed state by the insertion of an obturator for insertion through the stoma. Once the retaining element passes through the stoma the obturator can be removed allowing the retaining element to assume an enlarged state.

Some devices have been designed with areas of decreased thickness in the retaining element to enhance the collapsability of the retaining element during insertion or removal of the device. U.S. Pat. No. 5,336,203 to Goldhardt et al. discloses one such gastrostomy device in which the sidewall of a domed retaining element is thinned to enhance the collapsability of the device. U.S. Pat. No. 5,356,391 to Stewart discloses a gastrostomy tube having reinforced areas over portions of a hemispherically shaped retaining flange to enhance the collapsibility of the flange for atraumatic removal of the device. While enhancing collapsibility, these devices also have lessened resistance to inadvertent pull-out. A need remains for new devices which can be atraumatically inserted and removed through a stoma but which are also structured to reliably resist inadvertent pull-out.

SUMMARY OF THE INVENTION

The present invention generally provides new and useful medical devices which are particularly useful for long-term enteral feeding of a patient.

By one aspect of the present invention, there is provided a long term indwelling catheter with an improved one-way entrance seal module which will remain positively sealed closed after repeated and extensive use. The improved seal is especially useful when used as part of a low profile enteral gastrostomy feeding port where the valve and port might be left indwelling in a patient for up to a year and where a positive seal must be maintained even after hundreds of repeated uses.

The seal module includes a valve housing and a resilient valve member contained therein. The valve housing defines an inner passageway to provide fluid communication into a long term indwelling catheter and includes a rigid compression collar portion which defines a valve member receiving cavity within the inner passageway. In one aspect, the resilient valve member has a diaphragm portion which has an "S" shaped slit therein and an outer peripheral edge which generally conforms in shape to the valve member receiving cavity but is larger in dimension than the cavity when uncompressed. The resilient valve member also includes an outer wall portion which extends away from the outer peripheral edge of the diaphragm portion and which generally conforms in shape to the cavity. The resilient valve member is compressively fitted within the receiving cavity by the advancing of the outer wall portion into said cavity to thereby cause the outer peripheral edge to be compressed in dimension to fit within the cavity, with the compression collar pressing inwardly against the outer peripheral edge of the diaphragm portion to apply laterally compressive forces which bias the slit toward a normally closed position.

The resilient valve member is made of a one-piece resiliently molded valve with a flat membrane. The "S" shaped slit therein is formed by two arcically shaped leaves. The valve member is cylindrically shaped and is compressively fitted into the likewise cylindrically shaped compression collar to bias the arcical leaves to a positively sealed closed position. Feeding adapters can be repeatedly inserted through the valve and connected directly with the catheter lumen to deliver unobstructed enteral formula directly into the patient. Removal of the adapter returns the valve immediately to its positively sealed position due to the compressive forces of the collar about the arcically shaped leaves.

The valve remains compressively biased towards its sealed closed position when not in use, and is not permitted to stretch or deform which can lead to leakage. The one-way entrance seal permits convenient insertion of an obturator to help in insertion of the catheter into the body and the seal also permits convenient insertion of a feeding adapter which can be used for either feeding or decompression of the stomach. It needs no separate closure plug, or removal of a screw cap, or different feeding adapters, or complicated decompression tubes. This valve structure allows the device to be lower in profile and closer to the skin surface, and helps to make the device more convenient, less complicated, and easier to use than other devices in the prior art. The device is especially useful for active children who require low profile feeding ports.

Briefly describing another aspect of the present invention, ports are provided for accessing the interior of a body cavity or organ which is self retaining and resist inadvertent pull-out but that can be atraumatically implanted and removed. The devices include a retaining element which is resiliently deformable between a normally enlarged state for retention and a collapsed state for insertion and removal through a stoma and are provided with means for controllably biasing the element toward a longitudinal axis for collapsing the element.

A gastrostomy port device includes a port head defining a passageway having a first end and a second end and an entrance in communication with the first end of the passageway for receiving a delivery device. A hollow tubular stem portion having an inner end and an outer end is attached to the port head. The stem portion defines a lumen in communication with the second end of the passageway. The stem portion is sized to extend through the stoma with the port head disposed on the exterior of the patient. A retaining element is provided which has a first end attached to the inner end of the stem portion and a second end. The element defines a cavity in communication with the lumen and a hole in communication with the cavity for delivering materials to the interior of the body cavity. The element also has an interior surface defining a tool engaging surface at the second end of the element for engaging an insertion tool that passes through the lumen. The element is resiliently deformable between a normally enlarged state for retention and a collapsed state for insertion and removal through the stoma. The element includes a support surface at the first end configured for contacting the internal surface of the body cavity to retain the element within the body cavity when the stem portion is inserted through the stoma and the element is in its normally enlarged state.

In one feature of the invention, the interior surface of the element defines a first groove substantially parallel to a longitudinal axis defined by the cavity. The first groove is configured to controllably bias the folding and collapsing of the retaining element toward and generally parallel to the longitudinal axis when the insertion tool is engaged to or pressed against the tool engaging surface for insertion through the stoma.

Additional embodiments are disclosed which provide for the direct convertion of an implanted PEG tube to a low profile long term feeding device, and which further provide for the direct secure connection to an enteral feeding adapter without the need for an extension tube as an intermediate connector.

Accordingly, it is an object of the present invention to provide improved one-way entrance seals for medical catheters and gastrostomy feeding ports.

Another object of this invention is to provide a securely self-retaining gastrostomy port which can be atraumatically implanted and removed.

Still another object of the invention is to provide a low profile gastrostomy feeding port which incorporates a one-way seal and which provides for the securely sealed direct connection to an enteral feeding adapter.

Another object of the present invention is to provide a gastrostomy feeding port which is less complicated, easier to use, and less expensive than other commercially available products.

One advantage of this invention is that it provides self-retaining, atraumatic and anti-reflux features without the cumbersome and inconvenient aspects of prior devices.

Another object of the invention is to provide an improved gastrostomy feeding device utilizing a one-way seal that usefully converts an implanted PEG tube into a low profile feeding device.

Other objects, features, and advantages of the invention shall become apparent from the detailed drawings and descriptions which follow.

DESCRIPTION OF THE PREFERRED EMBODIMENT

Figure 1:
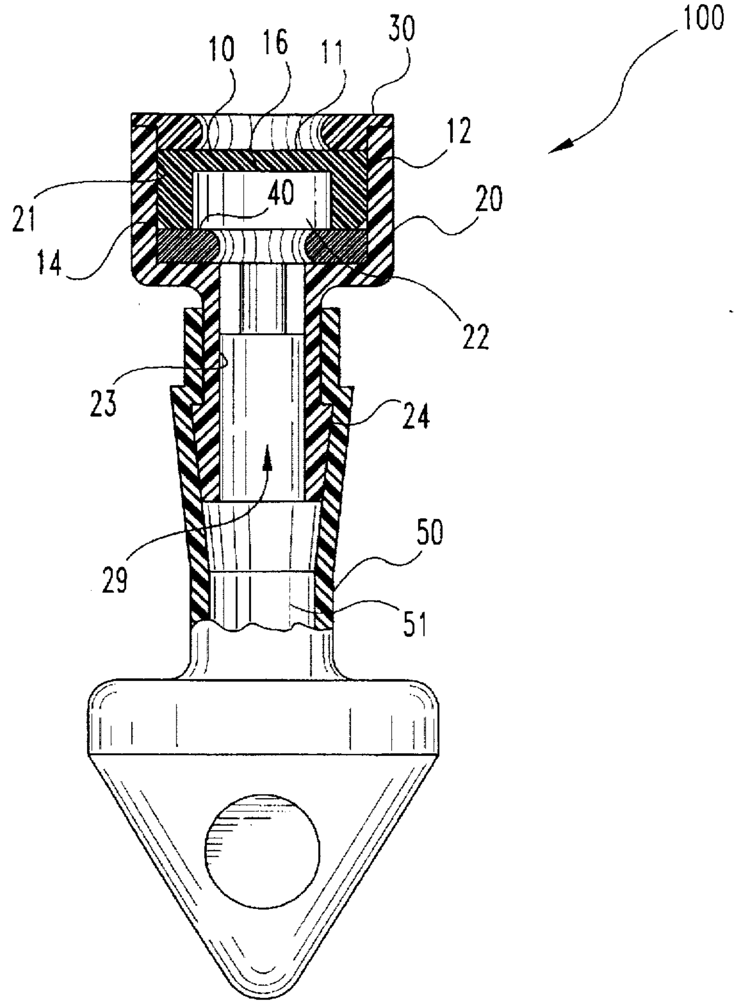
FIG. 1 is a side, partially cross-sectioned view of a gastrostomy port of the present invention incorporating a positively sealing one-way entrance valve.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 2:
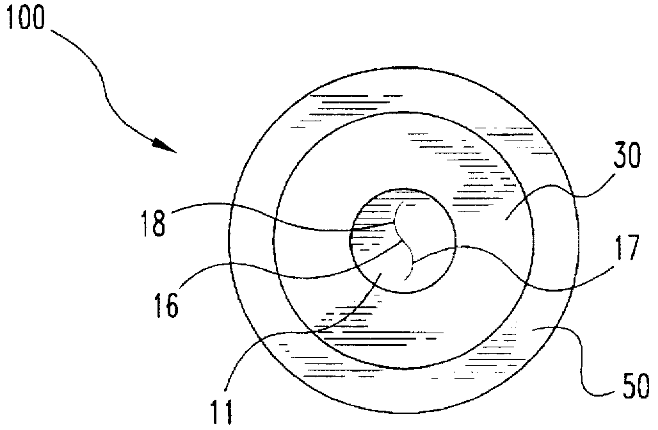
FIG. 2 is a top plan view of the gastrostomy feeding port of FIG. 1.

Referring now to FIGS. 1 and 2, there is shown a gastrostomy feeding port 100 which includes resilient valve member 10, valve housing 20, retainer cap 30, o-ring seal 40, and tubular/tip member 50. Resilient valve member 10 is made of silicone rubber, and has been constructed as a molded one-piece component and is preferably made from shore A 50 to 60 durometer high tear strength medical grade silicone. Diaphragm portion 11 of valve 10 is about 0.050 inches thick and about 0.325 inches in diameter and has a centrally located S-shaped slit 16 therein. Valve member 10 further has an outer cylindrical wall portion 12 which extends downwardly from the peripheral edge of diaphragm portion 11. O-ring 40 is preferably made of medical grade silicone as well, in the range of shore A 60 to 65 hardness.

Valve housing 20 defines an inner passageway 29 therethrough and includes rigid compression collar portion 21 which defines receiving cavity 22, annular seating portion 23 for seating of an adapter, and annular barb 24 for securing attachment to tubular/tip member 50. Valve housing 20 is injection molded from a rigid plastic such as lexan or polypropylene, but could be a machined part of stainless steel, or made of other suitable biocompatible material as well. Retainer cap 30 is preferably made of the same material as valve housing 20.

To assemble the valve structure for gastrostomy port 100, o-ring seal 40 is first placed into cavity 22 defined by compressive collar portion 21 of valve housing 20. Valve member 10 is then "press" fit into valve housing 20 by first fitting outer cylindrical wall portion 12 of valve member 10 into compression collar 21 and then applying even pressure to advance valve member 10 into cavity 22. The lower portion of cylindrical wall portion 12 of valve member 10 has a chamfered edge 14 to facilitate the introduction of valve member 10 into cavity 22. Also, isopropyl alcohol, which readily evaporates, can be used as a lubricant to aid in the press fitting of valve member 10 into valve housing 20.

As valve member 10 is advanced into cavity 22, cylindrical wall portion 12 is compressed to conform to the size of cavity 22. The compression of cylindrical wall portion 12, in turn, applies an evenly distributed compressive force on diaphragm portion 11 to cause diaphragm portion 11 to be evenly compressed and to thereby fit within cavity 22 without buckling or distorting. Once valve member 10 has been fully seated into valve housing 20, compression collar 21 acts with an inwardly directing compressive force to actively bias leaves 17 and 18 of "S" slit 16 on diaphragm portion 11 to positively seal valve member 10.

After valve member 10 has been seated into cavity 22, retainer cap 30 is placed on the top portion of valve housing 20 and affixed thereto. Attachment may be made by use of a suitable biocompatible solvent cement, or by ultrasonic welding. Once in place, retainer cap 30 does not exert any axial compressive force upon valve member 10, which could cause distortion of the sealing arrangement, and preferably only rests on the surface of diaphragm portion 11 or allows for a small gap therebetween.

Compression collar 21 supplies an interference fit of 0.015 inches around the entire circumference of cylindrical wall portion 12 and thus exerts an even sealing pressure on the S-slit 16 at all times. Compression collar 21 exerts this constant pressure or pre-load on leaves 17 and 18 to prevent diaphragm portion 11 from stretching or losing its resiliency when the valve is repeatedly opened or closed. Once assembled as described above, gastrostomy port 100 becomes one unitized piece with a one-way entrance valve seal accessing the central lumen of the tubular/tip member 50. The one-way valve permits only entrance into central lumen 51 and prevents any fluid from refluxing or backing up the tube and out the entrance seal.

Figure 3:
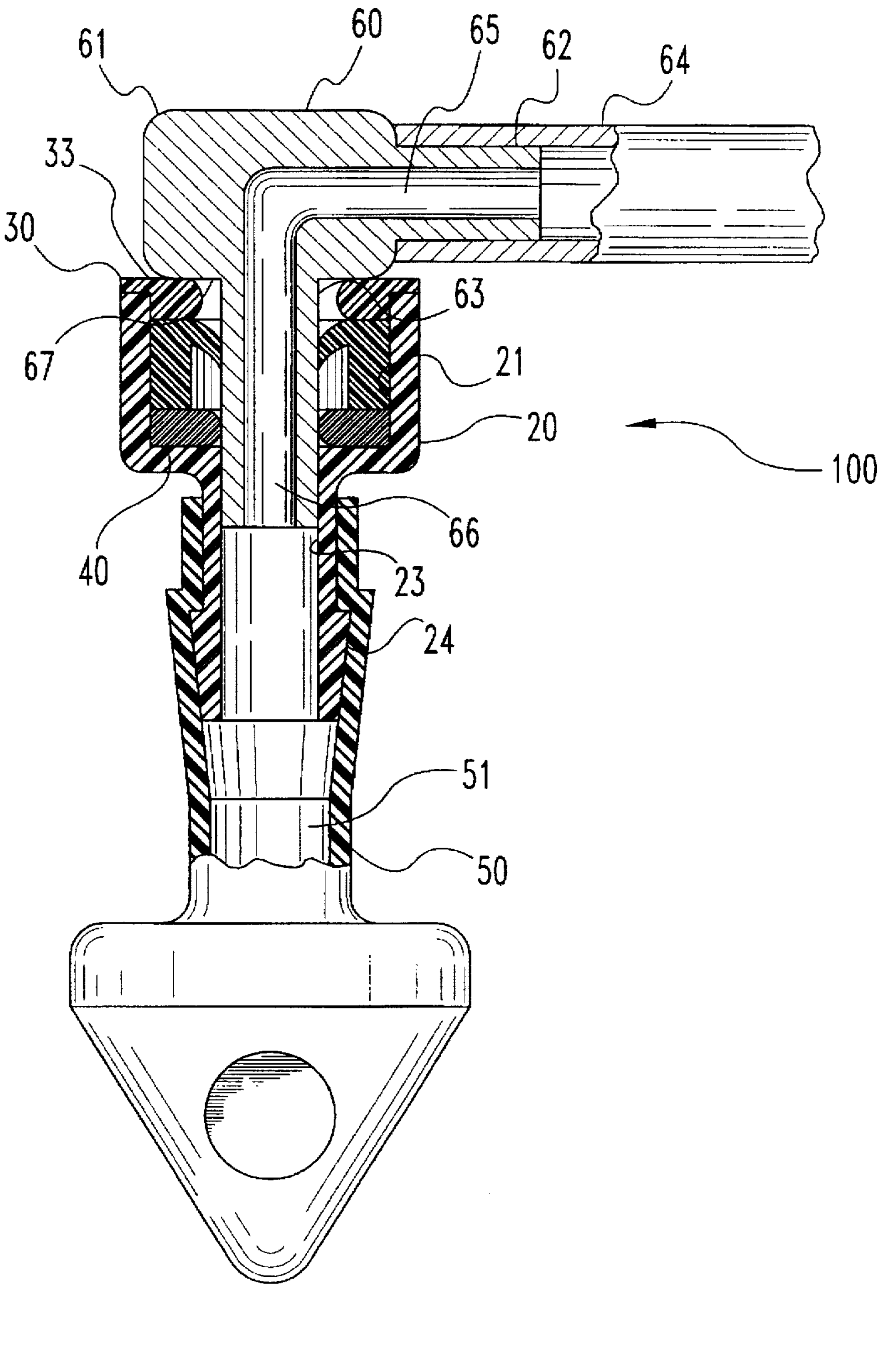
FIG. 3 is a partially cross-sectioned side view of the gastrostomy feeding port of FIGS. 1 and 2, showing a right angle adapter opening the one-way entrance seal and seated within the valve module to provide access into the catheter lumen of the feeding port.

FIG. 3 shows right angle adapter 60 opening entrance "S" slit 16 of valve member 10. Adapter 60 has a rigid injection molded right angle body portion 61, with rear stem 62 and front stem 63. Connected onto rear stem 62 is flexible PVC connecting tube 64. Rear stem 62 has lumen 65 and front stem 63 has lumen 66. When front stem 63 opens entrance seal 10, it seats into annular seating portion 23 of housing member 20. The underside surface 67 on right angle body portion 60 seats firmly on top surface 33 of retainer cap 20. So positioned, lumen 66 of front stem 63 accesses central lumen 51 of tubular/tip member 50. Right angle adapter 60 thus accesses lumen 51 of tubular/tip member 50 to deliver enteral formula or the administration of liquid medication into the body of a patient.

Adapter 60, via connecting tube 64, can be attached to any medication or enteral delivery set whether administered by gravity or a pump delivery method. In addition, adapter 60 can act as a decompression tube to vent gastrostomy port 100 and relieve pressure build up which tends to occur when a gastrostomy feeding port is left in place over a long period of time. When not in use, adapter 60 is removed and valve member 10 closes instantaneously to prevent reflux. Sealing is instantaneous due to compression collar 21 which acts to positively return leaves 17 and 18 to their normally closed position. Adapter 60 can be repeatedly inserted as needed over many months of use without the valve leaking or stretching out of shape.

As described above, a right angle adapter can be inserted into the valve S-slit 16 as needed. The valve remains in its normally closed positively sealed position due to compressive collar 21 acting to bias valve member 10 closed and keeping it closed to prevent reflux of stomach contents out through valve member 10. As such, feeding port 100 requires no internal anti-reflux valve, which might become clogged or stuck. It also does not need any removable valve cap or any stoppers or back up closure caps to add bulk to the outside profile. All functions can take place directly through the entrance seal, thus eliminating the need for anti-reflux valves, valve caps, stoppers, closure caps, or complicated decompression tubes.

Figure 4A:
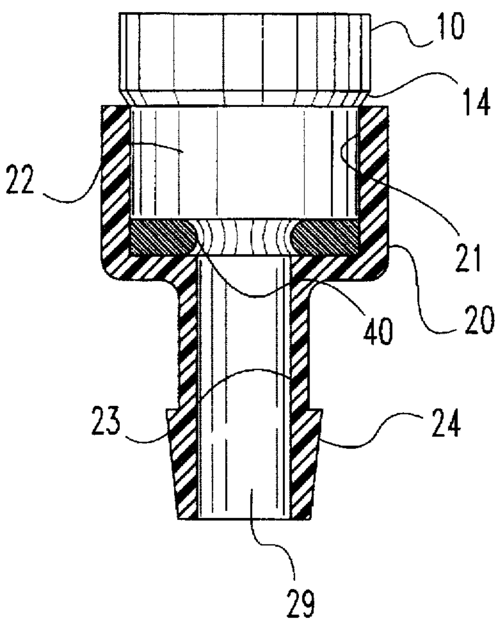
FIG. 4*a* is a side cross-sectioned view of the valve housing of FIGS. 1–3, showing resilient valve member 10 prior to positioning within cavity 22.
Figure 4B:
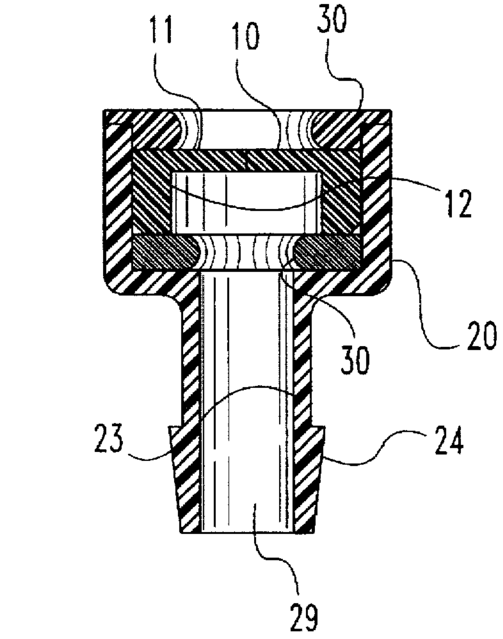
FIG. 4*b* is a side cross-sectioned view of valve housing 20 of FIG. 4*a*, showing resilient valve member press fitted into cavity 22, with retainer cap 30 mounted thereon to maintain valve member 10 within cavity 22.

FIG. 4*a* shows resilient valve member 10 prior to positioning within cavity 22. In FIG. 4*a*, valve member 10 is uncompressed and is larger in dimension than cavity 22. FIG. 4*a* further shows how chamfered edge 14 allows for the introduction of cylindrical wall portion 12 into cavity 22 such that valve member 10 can then be press fit into cavity 22 without buckling or distorting diaphragm portion 11. FIG. 4*b*, showing resilient valve member 10, after it has been press fitted into cavity 22, with retainer cap 30 mounted thereon to maintain valve member 10 within cavity 22.

Figure 5:
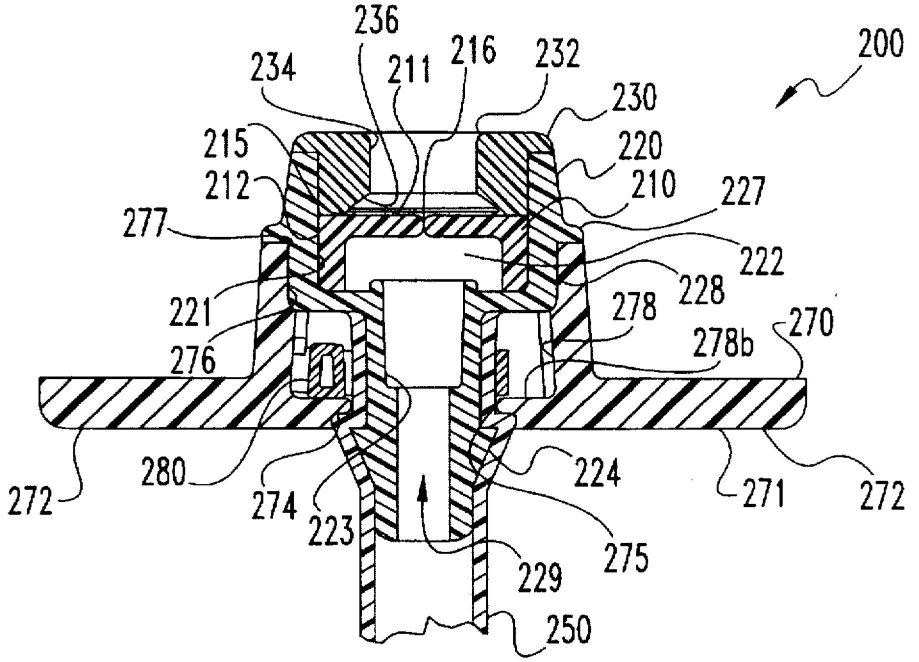
FIG. 5 is a side, cross-sectioned view of a second embodiment of the present invention which usefully converts an implanted PEG feeding tube into a low profile device, and which also directly connects to an enteral feeding adapter without the need for intermediate extension tubing.
Figure 6:
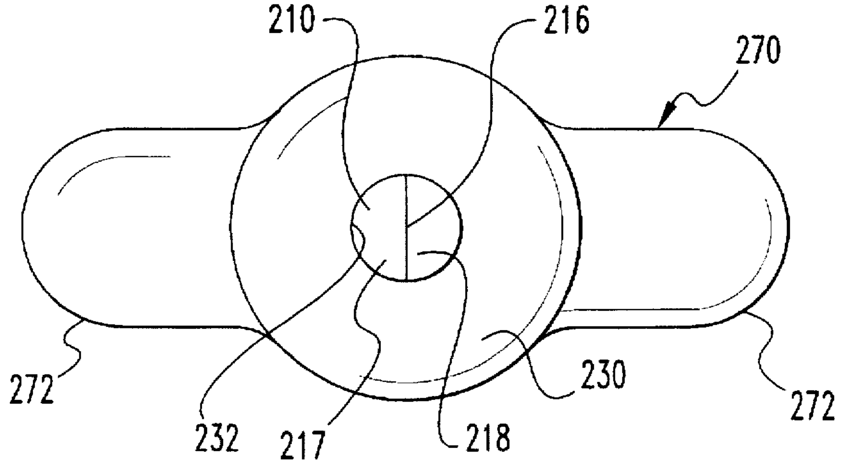
FIG. 6 is a top plan view of the gastrostomy port shown in FIG. 5.
Figure 7:
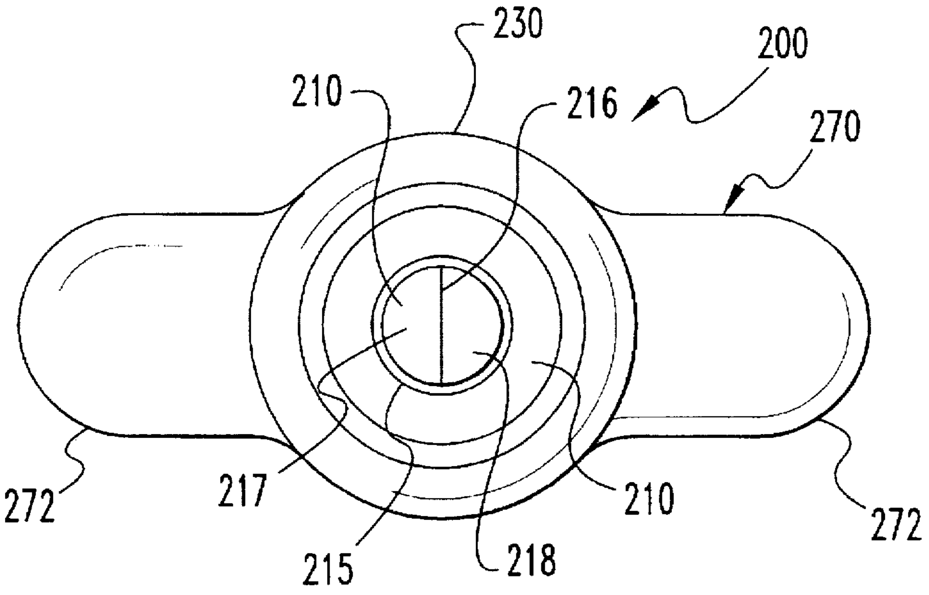
FIG. 7 is a top plan view of the gastrostomy port shown in FIG. 5 with the cap removed.

A second embodiment of the present invention is illustrated in FIGS. 5, 6 and 7 by which a long smooth walled PEG tube that has been previously implanted into a patient can be directly converted to a low profile gastrostomy port. By this conversion, the need to remove the PEG tube and install a separate low profile port is eliminated, thus making the procedure a simpler one for the physician while also reducing the added risk of infection and trauma attendant with complete replacement. Low profile conversion gastrostomy port 200 is also configured to directly connect to an enteral feeding adapter without the need for extension tubing.

Referring to FIG. 5, gastrostomy feeding port 200 is shown which includes resilient valve member 210, valve housing 220, retainer cap 230, and bolster 270, which are collectively connected to PEG tube 250. PEG tube 250 is a common smooth walled PEG tube which has been cut to a suitable length as part of the conversion process. Resilient valve member 210 is made of silicone rubber and has been constructed as a molded one-piece component and is preferably made from shore A 50 to 60 durometer high tear strength medical grade silicone. Resilient valve member 210 includes a diaphragm portion 211 which has a centrally located slit 216 therein. Valve member 210 further has an outer cylindrical wall portion 212 which extends downwardly from the peripheral edge of diaphragm portion 211. Also, valve member 210 includes a contact ring 215 about diaphragm portion 211. Contact ring 215 is more fully depicted in the top plan view of FIG. 7 which has cap 230 removed.

Referring again to FIG. 5, valve housing 220 defines an inner passageway 229 therethrough and includes rigid compression collar portion 221 which defines receiving cavity 222, annular seating portion 223 for seating of an adapter, and annular barb 224. Valve housing 220 also includes a base portion 228 with annular flange 227. Valve housing 220 should be made from a rigid biocompatible material, such as rigid PVC.

Retainer cap 230 defines a top opening 232 intersecting a passage 234 which, in turn, intersects cap cavity 236. Preferably, opening 232, passage 234, and cap cavity 236 are annular. Retainer cap 230 is preferably made of a shore A 70 to 75 durometer semi-rigid PVC, but could be made from another suitable biocompatible material as well. FIG. 6 provides a top plan view of cap 230 assembled on gastrostomy port 200.

Referring again to FIG. 5, gastrostomy feeding port 200 also includes bolster 270 with lower surface 271 and opposing tabs 272. Bolster 270 has an annular wall 276 which forms a chamber 278 opposing surface 271. Chamber 278 has upper opening 277 and is configured to receive valve housing 220. Annular wall 276 adjacent upper opening 277 forms a seal with the valve housing base 228 and abuts annular flange 227. Bolster 270 defines a lower opening 274 intersecting chamber 278 opposite upper opening 277. Lower opening 274 is configured to receive the severed end of PEG tube 250. Sealing ring 275 surrounds opening 274 and reinforces it to make it suitable for press-fit sealing. Bolster 270 is configured so that sealing ring 275 stretches over annular barb 224 with PEG tube 250 thereon and rebounds to clamp PEG tube 250 between sealing ring 275 and annular seating portion 223. Bolster 270 is thus configured so that sealing ring 275 clamps above annular barb 224 when annular wall 276 abuts annular flange 227. Furthermore, when so configured, annular wall 276 seals against housing base 228. The expansive area of surface 271 helps prevent inward migration of the gastrostomy port 200 into the body of a patient. The seal at opening 274 via sealing ring 275 further acts to sealingly prevent foreign materials and fluids from migrating along the outer surface of the PEG tube 250 and into gastrostomy port 200.

Figure 8:
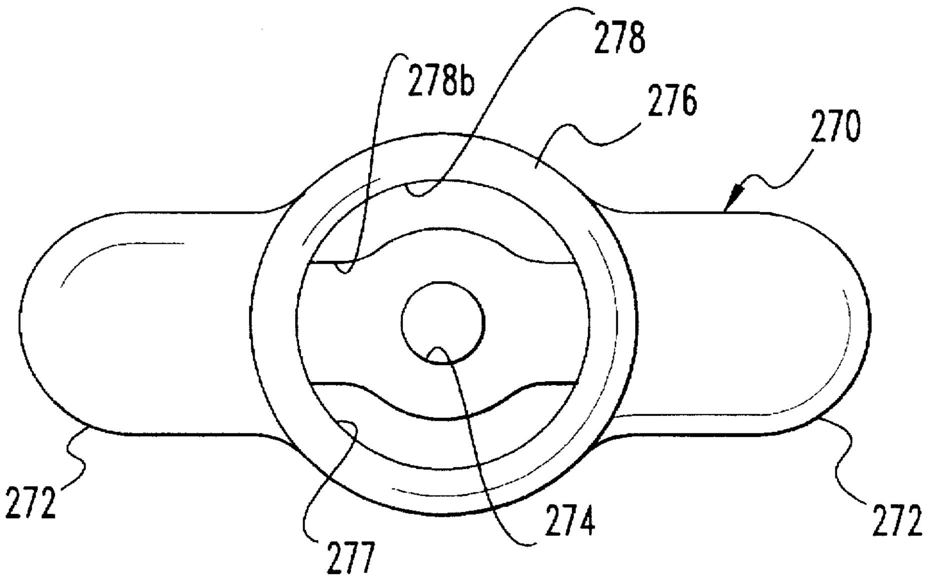
FIG. 8 is a top plan view of the bolster included in the embodiment shown in FIG. 5.

Referring to FIG. 8 as well as FIG. 5, chamber 278 includes a lower chamber portion **278*b*. Lower chamber portion 278*b* contains pull tie 280. Pull tie 280 is of a type known to those of skill in the art having an elongate band portion to encircle an object and an engagement mechanism to secure pull tie 280 to the object. Pull tie 280 encircles PEG tube 250 above annular barb 224 to secure it against annular seating portion 223. Preferably, bolster 270 is made of the same silicone material as the valve member 210 and cap 230**.

To assemble the valve structure for gastrostomy port 200, valve member 210 is "press" fit into valve housing 220 similar to the method described for gastrostomy port 100 (see FIGS. **4*a* and 4*b* and accompanying text herein), with ring 215 of valve member 210 facing upward as shown in FIG. 7. Also, slit 216, which is generally straight configuration, is biased towards a positively sealing closed position by the inwardly directed compressive force from collar 221 which actively biases slit 216 to positively seal valve member 210. Compression collar 221 exerts this constant pressure or pre-load on slit 216 to prevent diaphragm portion 211** from stretching or losing its resiliency when the valve is repeatedly opened or closed.

After valve member 210 has been seated into cavity 222, retainer cap 230 is placed on the top portion of valve housing 220 and affixed thereto by solvent cementing or such other biocompatible bonding method appropriate for joining retainer cap 230 and valve housing 220. Cap wall 236 engages contact ring 215 of valve member 210 to seal guard against leakage under cap 230. Once in place, retainer cap 230 does not exert any axial compressive force upon valve member 210, which could cause distortion of the sealing arrangement. Contact ring 215 provides reinforcement about diaphragm portion 211 and so assists in preventing distortion of the sealing arrangement.

To accomplish the conversion of PEG tube 250 to a low profile feeding port, PEG tube 250 is first clamped and then severed at an appropriate length near the stoma opening. Preferably the length of the cut tube should allow for some free-play between bolster surface 271 and the portion of the PEG tube 250 entering into the stoma site. A preferred range is 1 to 5 centimeters with a more preferred range of 1.5 to 3 centimeters and a most preferred value of about 2 centimeters.

Bolster 270 is then placed on PEG tube 250 working PEG tube 250 through opening 274 until the end of the PEG tube 250 extends beyond opening 277. Annular seating portion 223 is then inserted into PEG tube 250 until the end of PEG tube 250 goes past the annular barb 224 and rests adjacent housing base 228. Pull tie 280 is placed about PEG tube 250 between housing base 228 and annular barb 224 and is pulled to clamp PEG tube 250 between it and annular seating portion 223 of valve housing 220. Pull tie 280 includes a mark placed along a given length of the elongate band portion for alignment with the engagement mechanism. This mark is positioned to correspond to the proper length of pull tie 280 to assure that adequate tension is exerted to the PEG tube 250 for a reliable seal. Consequently, by aligning this mark appropriately, the proper amount of clamping force results and a reliable seal of PEG tube 250 to annular seating portion 223 is consistently obtained. Any extraneous portion of pull tie 280 is then removed by cutting and trimming the excess as close to the engagement mechanism as possible.

Next, bolster 270 is moved along PEG tube 250 until annular wall 276 abuts annular flange 227, receiving housing base 228, and sealing ring 275 is above annular barb 224. Tabs 272 provide a convenient point to manipulate bolster 270. As a result, pull tie 280 is enclosed within lower chamber portion **278*b* so that bolster 270 protects the patient from unpleasant contact therewith and at the same time provides a relatively large surface area to abut the patient's skin and shelter the passage in the patient's body which contains PEG tube 250**.

As assembled as described above, gastrostomy port 200 provides a low profile gastrostomy port with a one-way entrance valve seal accessing the central lumen of the PEG tube 250. Gastrostomy port 200 is especially useful for directly converting a PEG tube to a low profile gastrostomy port device. Gastrostomy port 200 provides a secure and reliable connection to PEG tube 250. Furthermore, the one-way valve only permits entry and prevents fluid from refluxing or backing up the tube and out the entrance seal. Also, gastrostomy port 200 can be directly connected to a standard enteral feeding adapter as shown in FIG. 11, thus eliminating the need to use intermediate extension tubing.

Figure 9:
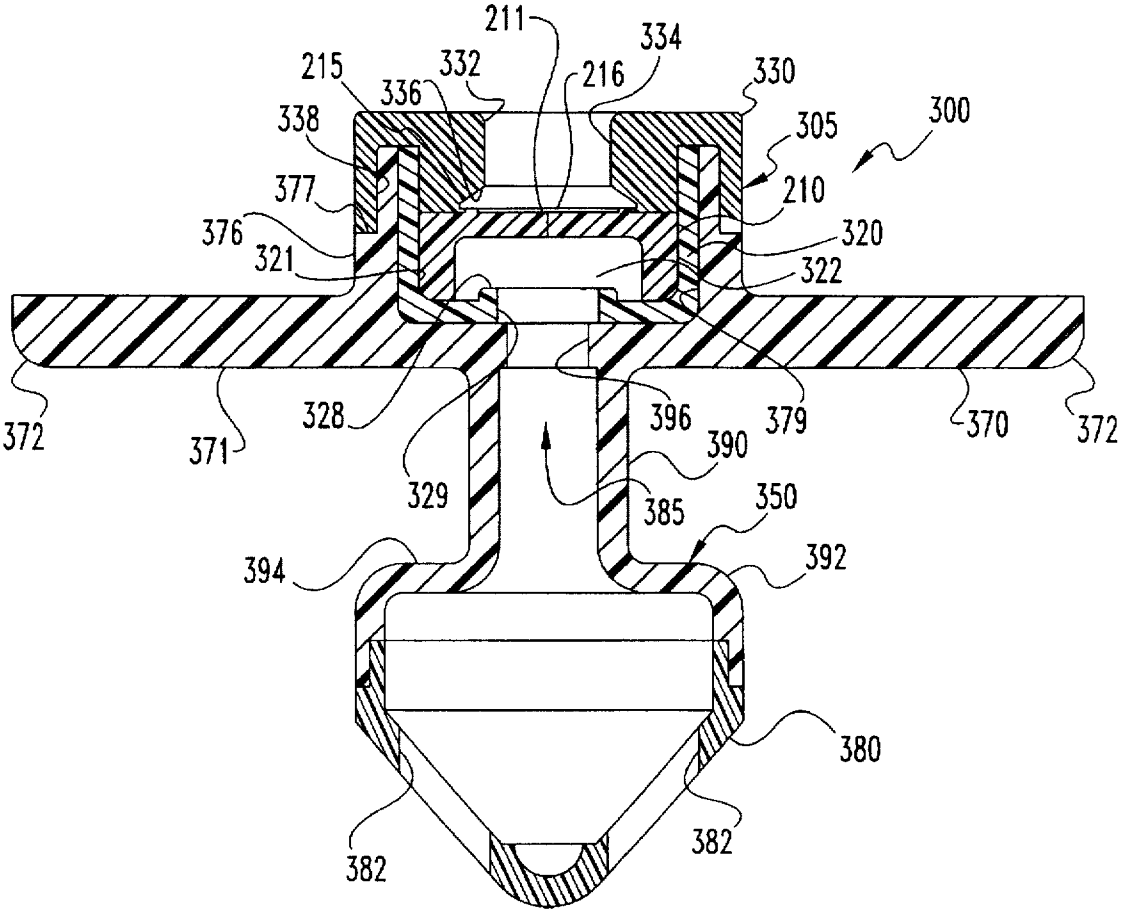
FIG. 9 is a side, cross-sectioned view of a third embodiment of a unitary, fixed length, low profile gastrostomy port of the present invention which directly connects to an enteral feeding adapter without the need for intermediate extension tubing.
Figure 10:
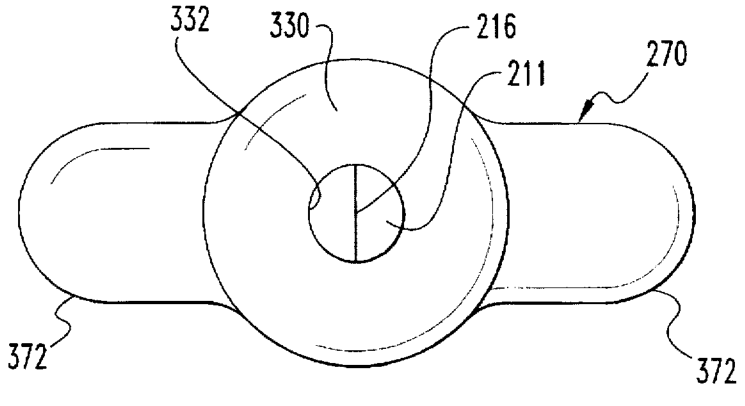
FIG. 10 is a top plan view of the gastrostomy port shown in FIG. 9.
Figure 11:
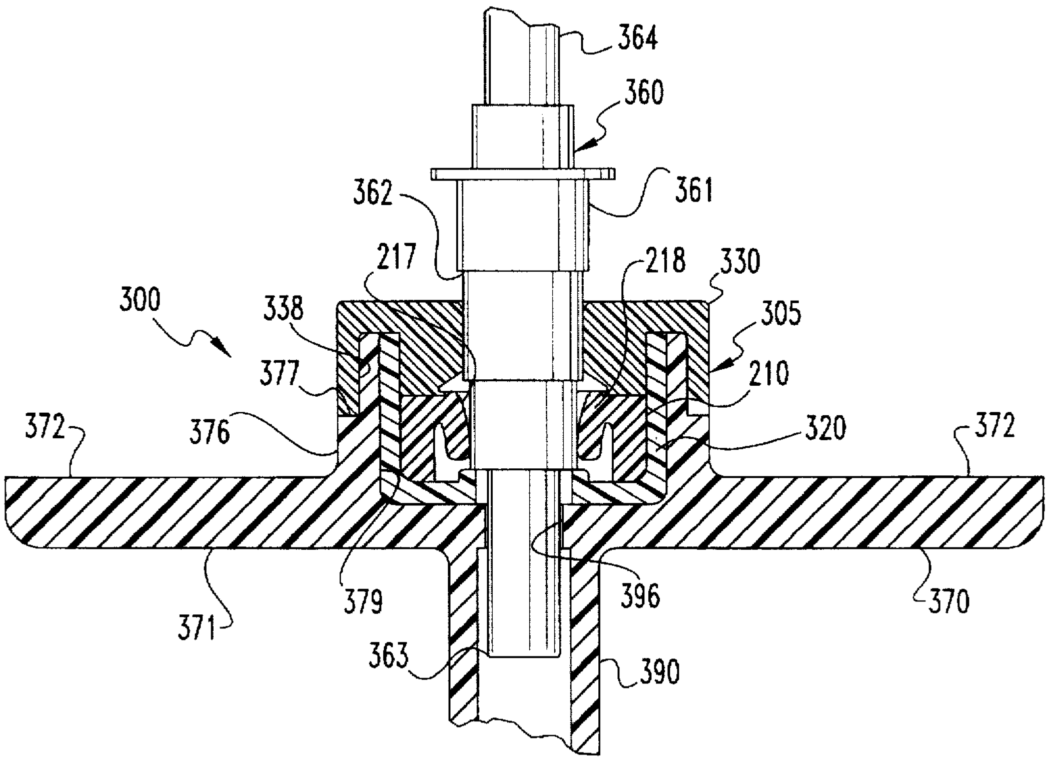
FIG. 11 is a partially cross-sectioned side view of an enteral feeding adapter directly connected to the gastrostomy feeding port of FIGS. 9 and 10.

Another embodiment of the present invention will now be described which provides a unitary fixed length low profile gastrostomy port, as illustrated in FIGS. 9, 10, and 11. Specifically, gastrostomy feeding port 300 is depicted which includes resilient valve member 210, valve housing 320, retainer cap 330, and main port body member 350. Resilient valve member 210 is the same valve member depicted in FIGS. 5–7.

Valve housing 320 defines a lower opening 329 therethrough and includes rigid compression collar portion 321 which defines receiving cavity 322. Valve housing 320 also includes a support base portion 328 adjacent opening 329. Valve housing 320 is injection molded from a rigid plastic such as lexan or polypropylene, but could be a machined part of stainless steel, or made of other suitable biocompatible material as well.

Retainer cap 330, which is made of silicone or other suitable biocompatible material, defines a top opening 332 intersecting passage 334 which, in turn, intersects cap cavity 336. Preferably, opening 332, passage 334, and cap cavity 336 are annular. Retainer cap 330 also defines an annular channel 338 configured to engage main port body member 350 and valve housing 320. Retainer cap 330 is preferably made of the same material as valve member 210.

Gastrostomy feeding port 300 also includes a unitary main port body member 350. Main port body member 350 is made of silicone or other suitable biocompatible material and has a conical tip portion 380 connected to tubular stem portion 390 by a biocompatible adhesive solvent or cement such as RTV. Tubular stem portion 390 has a bell shaped portion 392 with a surface 394 configured for contact against the wall of the patient's stomach. Preferably the length of stem portion 390 allows for some free-play of main port body member 350 implanted in the patient's stomach. A preferred range is 1 to 5 centimeters with a more preferred range of 1.5 to 3 centimeters and a most preferred value of about 2 centimeters. The conical tip 380 defines holes 382. Main port body member 350 defines a passage 385 intersecting the holes 382 and a tube opening 396 in coupling portion 370.

Tubular stem portion 390 is integrally connected to a coupling portion 370 with opposing flaps 372 which aid in the placement and manipulation of gastrostomy feeding port 300. Coupling portion 370 has a lower surface 371 which is configured to contact the patient's skin adjacent the passage in the patient's body containing the tubular stem portion 390. Coupling portion 370 also includes an upper annular wall 376 with an annular shelf 377. Annular wall 376 defines a space 379 for receiving valve housing 320 and is configured to engage annular channel 338 along side compression collar 321. The space 379 is further configured so that opening 329 aligns with tube opening 396 when the valve housing 320 is received therein.

To assemble the valve structure for gastrostomy port 300, valve member 210 is "press" fit into valve housing 320 similar to the method described for gastrostomy ports 100 and 200. Compression collar 321 exerts a constant pressure or pre-load on slit 216 to prevent diaphragm portion 211 from stretching or losing its resiliency after repeated use.

After valve member 210 has been seated into cavity 322, valve housing 320 is placed into space 379 of member 350. The conical tip 380 may be bonded to tubular stem portion 390 either before or after these steps. Next, retainer cap 330 is situated so that compression collar 321 and annular wall 376 engage annular channel 338 and retainer cap 330 abuts annular shelf 377. Once in position, retainer cap 330 is attached to member 350 by a biocompatible adhesive, such as an RTV. When so positioned, retainer cap 330 does not exert any axial compressive force upon valve member 310 which could cause distortion of the sealing arrangement. Together, retainer cap 330 and coupling portion 370 comprise a port head 305 which contains valve housing 320 and resilient valve member 210.

Gastrostomy port 300, as above described and shown in FIGS. 9, 10, and 11, provides a unitary fixed length low profile gastrostomy port with a one-way positively sealing entrance valve. The one-way valve permits only entrance into passage 385 and prevents any fluid from refluxing or backing up the tube and out the entrance seal. Gastrostomy port 300 can be used directly connected to a standard enteral feeding adapter as shown in FIG. 11.

FIG. 11 shows an adapter 360 opening entrance slit 216 of valve member 210 situated in gastrostomy port 300. Adapter 360 has a rigid injection molded body portion 361, with a passage through a base stem portion 362 and front stem portion 363. Connected onto base stem portion 362 is flexible PVC connecting tube 364.

Adapter 360 directly connects to the gastrostomy port 300. The front stem portion 363 passes through top opening 332 and opens valve member 210. Next, front stem portion 363 passes through opening 329, engages tube opening 396, and extends into passage 385. Tube opening 396 is configured so that it seals against front stem portion 363 positioned therein. Just as front stem portion 363 engages tube opening 396, the base stem portion seats against support base 328 of valve housing 320. Not only does support base 328 offer support to the adapter, but also prevents inserting the adapter too far into the gastrostomy port 300. In this supported position, the top opening 332 seals against the base stem portion 362 of adapter 360. Adapter 360 thus accesses passage 385 of member 350 to directly deliver enteral formula or the administration of liquid medication into the body of a patient having a lower seal at tube opening 396 and an upper seal at top opening 332. Between these two seals a support base is provided which limits the extent of penetration of adapter 360 into the gastrostomy port 300 and the valve member 210 opens to allow adapter 360 to pass therethrough. When adapter 360 is removed, valve member 210 closes instantaneously to prevent reflux. Sealing is instantaneous due to compression collar 321 which acts to positively return leaves 217 and 218 to their normally closed position. Adapter 360 can be repeatedly inserted as needed over many months of use without the valve leaking or stretching out of shape.

Figure 12:
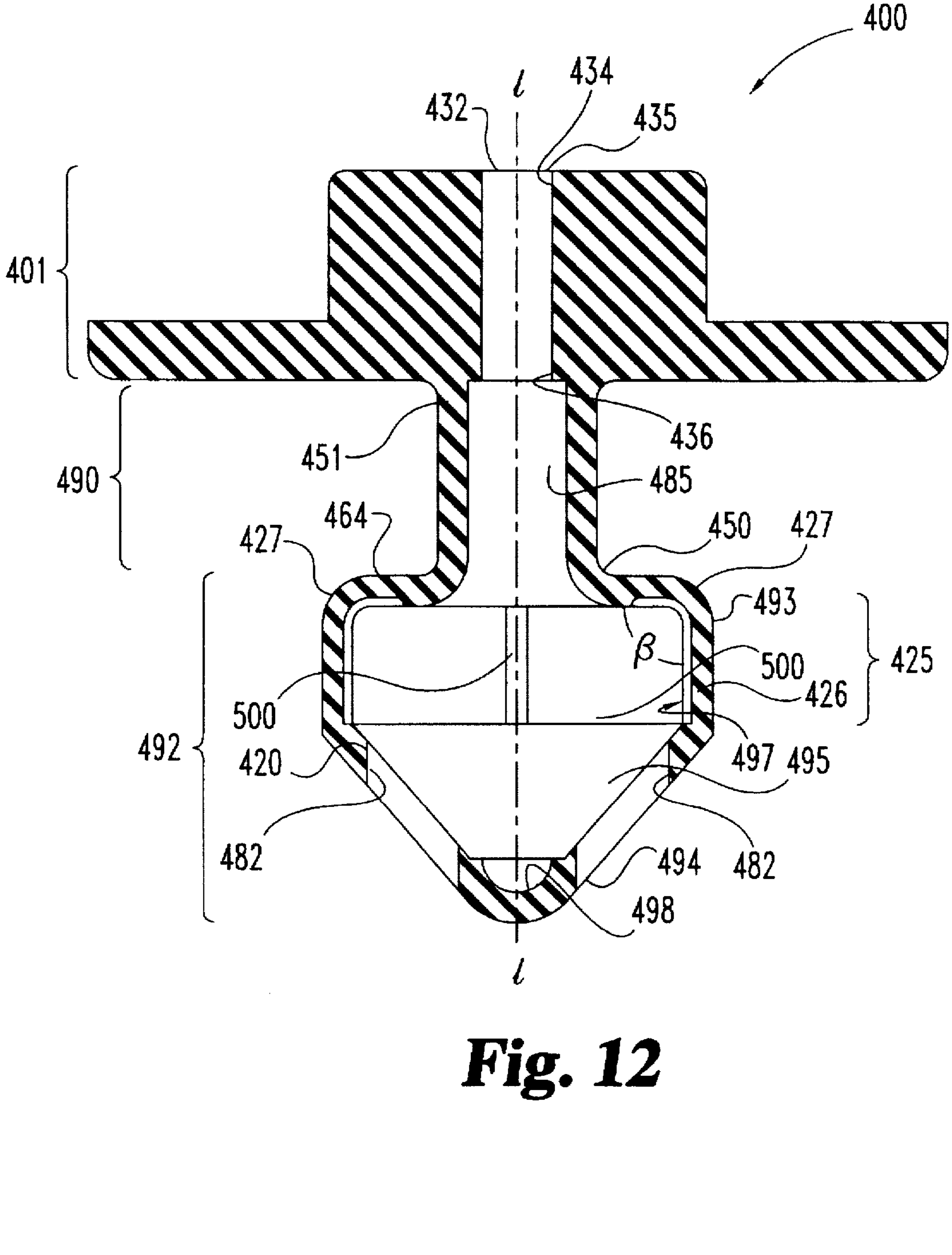
FIG. 12 is a side, cross-sectioned view of one embodiment of a port having a retaining element implanted within a stoma.
Figure 13:
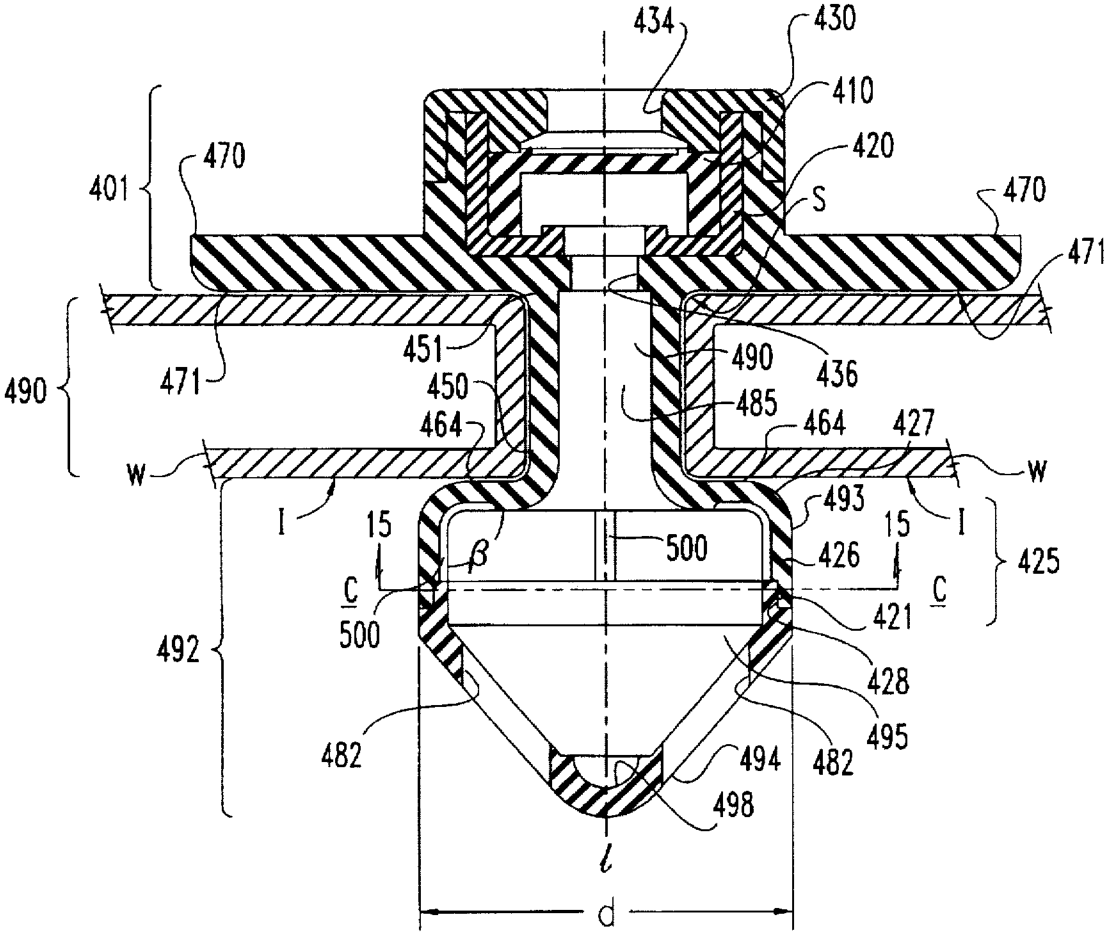
FIG. 13 is side, cross-sectioned view of a port having a one-way valve and a self-retaining element implanted within a stoma.

Devices are further provided, as shown in FIGS. 12–17, having features which enhance the atraumatic insertion and removal of the device through a stoma while also providing sufficient structure to reliably resist device pull-out. Like figure numbers for components of different embodiments in these drawings signify that the components correspond. As depicted in FIGS. 12 and 13, the present invention includes devices 400 for insertion into a stoma S through a wall W of a body cavity C of a patient for transport of materials from the exterior of the patient to the interior of the body cavity C. The device 400 includes a port head 401, a stem portion 490 and a retaining element 492. The port head 401 defines a passageway 434 having a first end 435 and a second end 436. An entrance 432 is in communication with the first end 435 of the passageway 434 for receiving a delivery device for delivery of nutrients and medicines.

FIG. 13 depicts a device similar to the port of FIG. 9 equipped with a retaining element 492 as shown in FIG. 12. The port head 401 of this embodiment includes a resilient valve member 410, a valve housing 420, a retainer cap 430 and a bolster 470 having lower surfaces 471 as described above. The device 400 also includes a hollow tubular stem portion 490 having an inner end 450 and an outer end 451 attached to the port head 401. The stem portion 490 defines a lumen 485 in communication with the second end 436 of the passageway 434. The stem portion 490 is sized to extend through the stoma S with the port head 401 disposed on the exterior E of the patient as shown in FIG. 13.

The device 400 also includes a retaining element 492 having an open first end 493 attached to the inner end 450 of the stem portion 490 and a closed second end 494. The element preferably includes a support portion 464 at the first end 493 for contacting the internal surface I of a body cavity C. The retaining element 492 defines a substantially enclosed cavity 495 in communication with the lumen 485 and a hole 482 in communication with the cavity 495 for delivering materials to the interior of the body cavity C.

In one preferred embodiment, the retaining element 492 includes a conical tip 420 opposite the support portion 464 and the hole 482 is defined in this tip 420. The retaining element 492 includes an interior surface 497 which defines a tool engaging surface 498 at the second end 494 of the retaining element 492 for engaging an insertion tool. Most preferably, the retaining element 492 includes a shoulder portion 425 which defines the support portion 464 and an annular wall portion 426 as shown in FIG. 13. The shoulder portion includes a bend 427 between the support portion 464 and the annular wall 426. In one preferred embodiment, the support portion 464, the bend 427 and the annular wall 426 form an angle β which is most preferably about 90 degrees. It is to be understood that alternative configurations for the retaining element 492 are contemplated as well which may suitably serve the purposes intended.

Figure 14:
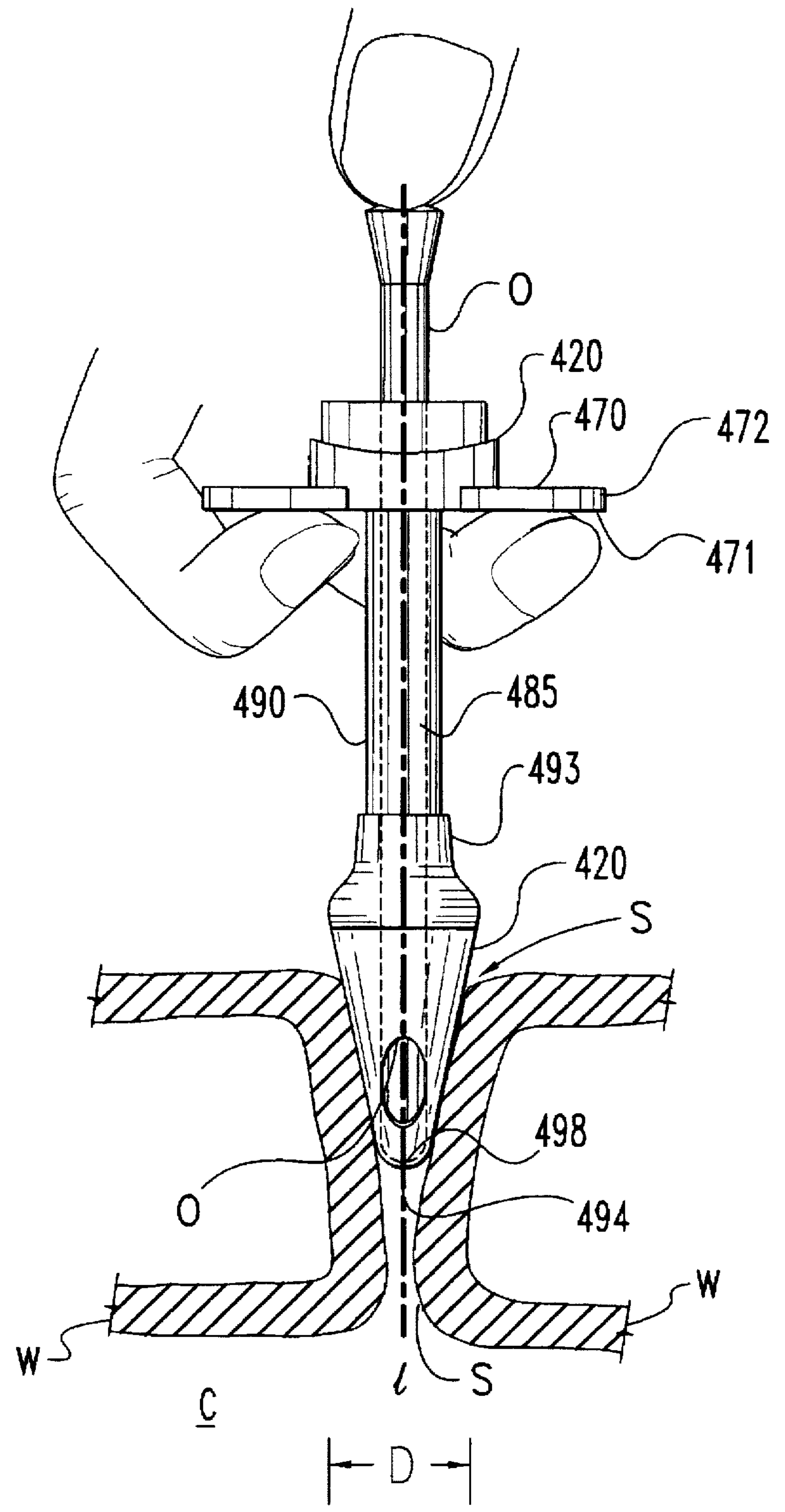
FIG. 14 depicts the implantation of the port depicted in FIG. 13 in the collapsed state using an obturator.

The retaining element 492 is made of a resilient, biocompatible, elastomeric material so that it is resiliently deformable between a normally enlarged state as shown in FIGS. 12 and 13 and a collapsed state as shown in FIG. 14 for insertion and removal through the stoma S. Any suitable resilient, biocompatible material having plastic memory is contemplated, such as polyurethane, rubber latex, styrene-butadiene-rubber latex and preferably, silicone rubber. When the stem portion 490 is inserted through the stoma S and the element 492 is in its normally enlarged state, the support portion 464 of the retaining element 492 is configured for contacting the internal surface I of the body cavity C to retain the element 492 within the body cavity C as shown in FIG. 13.

Devices of this invention are preferably provided with means for controlling the deformation of the retaining element 492 between the normally enlarged state (FIG. 13) for retention and the collapsed state (FIG. 14) for insertion and removal. For this purpose, grooves 500 in the retaining element 492 controllably bias the folding of the retaining element 492 during insertion and removal while also providing sufficient structure to reliably resist pull-out of the device 400.

Figure 15:
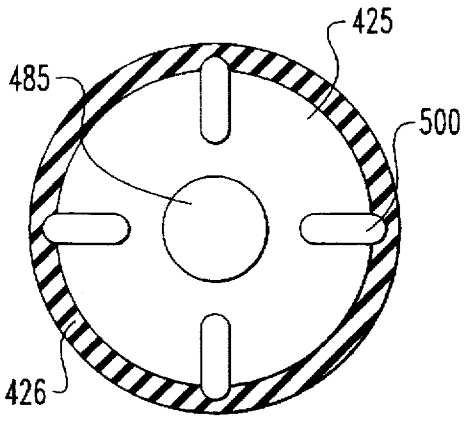
FIG. 15 is an end cross-sectional view of the retaining element depicted in FIG. 13 taken along lines 15—15.

In one preferred embodiment, the grooves are defined in the interior surface 497 of the retaining element 492. Preferably, the grooves 500 are defined in the shoulder portion 425 as depicted in FIGS. 12, 13 and 15. In a most preferred embodiment best shown in FIG. 16, each of the grooves 500 extend on the interior surface 497 from the annular wall 426, through the bend 427 and onto the support portion 464. Although the grooves 500 of the present invention bias the folding of the retaining element 492, they do not appreciably diminish rigidity. Advantageously, this invention enhances deformation of the retaining element 492 for insertion but resists inadvertent collapse that might occur from pulling on the device 400.

In one preferred embodiment, the retaining element defines four grooves in spaced relation, as shown in FIG. 15. Referring again to FIG. 12, the grooves 500 are substantially parallel to a longitudinal axis l defined by the cavity 495. When an insertion tool is engaged to and pressed against the tool engaging surface 498 for insertion through the stoma as shown in FIG. 14, the grooves 500 are configured, or shaped, sized and located, to controllably bias the folding and collapse of the retaining element 492 toward the longitudinal axis l. Particularly, it has been found that the retaining element will deflect inward or collapse at one or more of the grooves 500. It is contemplated that the insertion tool can be any mandrel-like tool such as an obturator.

Figure 17:
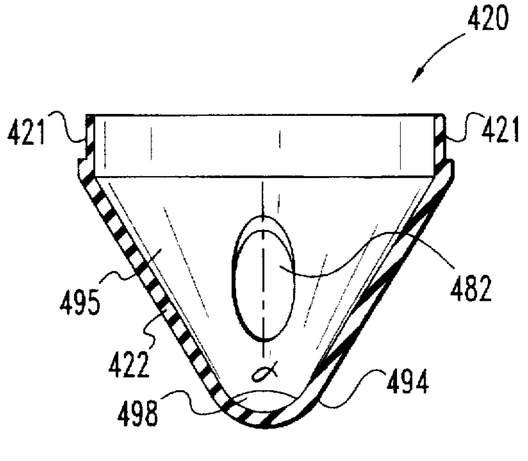
FIG. 17 is a front cross-sectional view of the tip of the retaining element depicted in FIG. 13.

In the embodiment shown in FIG. 17, each of the holes 482 are oval having a major axis α which is substantially parallel to the longitudinal axis l (FIG. 14). The holes 482 are of any suitable size and shape which provides free delivery of materials from the cavity 495 but which still maintain the structural integrity of the retaining element 492. In a preferred embodiment, two oppositely spaced holes 484 are defined in a conical tip portion 420 of the retaining element 492.

It is contemplated that the embodiment of the invention shown in FIG. 12 can be equipped with any suitable port head 401 and/or stem portion 490. For example, the retaining element 492 as shown in FIG. 12 can be placed in combination with the stem portions and port heads as shown in FIGS. 1 and 11.

Figure 16:
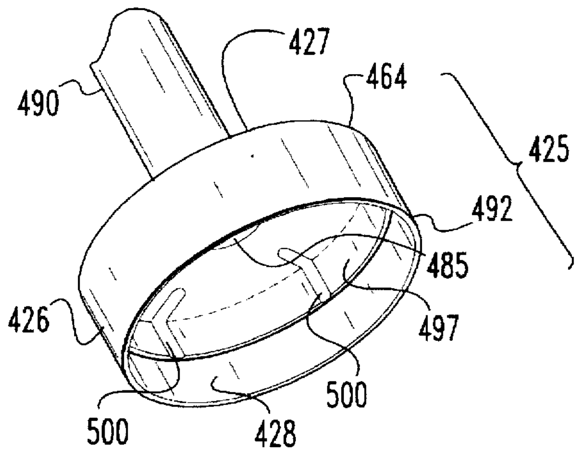
FIG. 16 is a bottom cross-sectional view of a portion of the device shown in FIG. 13.

In the preferred embodiment shown in FIG. 13, stem portion 490 and the annular wall 426 are integrally molded. The tip 420 is attachable to the annular wall 426, such as by bonding as discussed above. As shown in FIGS. 13, 16 and 17, the annular wall 426 may be provided with a bonding surface 428 defined by a cut-out in the annular wall 426. In this embodiment, the tip 420 would include a mating surface 421 defined by a complementary cut-out in the wall 422 of the tip 420 for securely attaching the tip 420 to the annular wall 426.

Prior to insertion into a stoma, device 400 is fitted with an insertion device such as the obturator O depicted in FIG. 14. With the valve 410, the valve housing 420 and the retainer cap 430 removed from the port head, (see FIG. 13) the obturator O is inserted into the passageway 434. While the port head 401 is supported by digital contact on the lower surface 471 of the bolster 470, the obturator O is extended through the lumen 485 of the stem portion 490 and into the cavity 495 of retaining element 492. The pressure of the obturator O against the tool engaging surface 498 of the interior surface 497 of the retaining element 492 causes deformation of the retaining element 492. As the device-obturator assembly is inserted through the stoma S, the traction force of the stoma S against the shoulder portion 425 in combination with the force of the obturator O against the tool engaging surface 498 is thought to cause collapse of the retaining element 492 at the grooves 500 as shown in FIG. 14. The most beneficial results have been found when the grooves 500 extend through the bend 427 on the interior surface 497 of the shoulder portion 425 of the element 492. The grooves 500 controllably bias the folding of the retaining element 492 to cause the uniform collapse of the retaining element 492 towards the longitudinal axis l for passage through the stoma S during insertion and removal.

With the retaining element 492 in a collapsed state as shown in FIG. 14, it can be atraumatically inserted through the stoma S and into the body cavity C. After the retaining element 492 is inserted through the stoma and into the body cavity, the obturator O is removed. When the obturator O is removed, the retaining element 492 returns to its normal enlarged state as shown in FIG. 13. In the normally enlarged state of the retaining element 492, the shoulder 425 of retaining element 492 has an effective diameter d which is greater than the diameter D of the stoma S. As shown in FIG. 13, the support portion 464 contacts the interior surface of the body cavity. Once the insertion device is removed, the valve 410, valve housing 420 and retainer cap 430 are replaced and the port is ready to receive a delivery device. The retaining element 492 can be collapsed and atraumatically removed through the stoma S as described above for removal of the port.

As can be appreciated, a number of variations of the gastrostomy ports 100, 200, 300 and 400 can be made which fall within the underlying spirit of the invention. For instance, variations in form of the entrance seal can be made from that specifically described herein without departing from the spirit or scope of the underlying invention. Also, varying configurations as to the shape of the valve and corresponding valve receiving cavity, in the slit within the valve, or in the grooves within the retaining element may still fall within the spirit and scope of this invention. With the foregoing in mind, it is apparent to those skilled in the art to make modifications or different configurations of the invention without varying from the invention and the invention is not to be limited to the particular forms herein shown and described except insofar as indicated by the scope of the appended claims.

Accordingly while the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A device for insertion into a stoma through a wall of a body cavity of a patient for transport of materials from the exterior of the patient to the interior of the body cavity, comprising:

a port head defining a passageway having a first end and a second end and an entrance in communication with said first end of said passageway for receiving a delivery device;

a hollow tubular stem portion having an inner end and an outer end attached to said port head, said stem portion defining a lumen in communication with said second end of said passageway, said stem portion sized to extend through the stoma with said port head disposed on the exterior of the patient;

a retaining element having an open first end attached to said inner end of said stem portion and a closed second end, said element defining a substantially enclosed cavity in communication with said lumen and a hole in communication with said cavity for delivering materials to the interior of the body cavity, said element having an interior surface defining a tool engaging surface at said second end of said element for engaging an insertion tool;

said element being resiliently deformable between a normally enlarged state for retention and a collapsed state for insertion and removal through the stoma, said element having a support portion at said first end of said element configured for contacting the internal surface of the body cavity to retain said element within the body cavity when said stem portion is inserted through the stoma and said element is in its normally enlarged state; and said interior surface of said element defining a first groove substantially parallel to a longitudinal axis defined by said cavity, said first groove configured to controllably bias the folding and collapse of said retaining element toward said longitudinal axis when the insertion tool is pressing against said tool engaging surface for atraumatic passage through the stoma.

2. The device of claim 1 wherein said internal surface further defines a number of grooves parallel to said longitudinal axis and in spaced relation to said first groove.

3. The device of claim 1 wherein said element includes a conical tip opposite said support portion and said hole is defined in said conical tip.

4. The device of claim 3 wherein said element includes a shoulder portion defining said support portion, an annular wall portion and a bend between said support portion and said annular wall portion, said shoulder portion defining said grooves, each said groove extending through said bend.

5. The device of claim 1 wherein said element includes a semi-spherical tip opposite said support portion and said hole is defined in said tip.

6. The device of claim 1 wherein said port head, said stem portion and said annular wall are integrally molded and said tip is attachable to said annular wall portion.

7. The device of claim 1 wherein said element is dome shaped when said element is in the enlarged state.

8. The device of claim 1 wherein said support portion is planar when said element is in the enlarged state.

9. The device of claim 8 wherein said support position, said bend and said annular wall form an angle when said element is in the enlarged state, said angle being about 90 degrees.

10. The device of claim 1 wherein said support portion is concave when said element is in the enlarged state.

11. The device of claim 1 wherein said hole is oval having a major axis, said major axis substantially parallel to said longitudinal axis.

12. The device of claim 1, wherein:

said entrance has a first diameter which allows a first distal portion of the delivery device to pass through into said passageway and which is sized to sealingly engage a larger second portion of the delivery device, said port head further defining a tube opening in communication with said second end of said passageway, said tube opening having a second diameter configured to sealingly engage the first portion of the delivery device.

13. The device of claim 1, wherein:

said port head further includes a one-way entrance valve including:

a rigid compression collar portion which defines a valve member receiving cavity;

a resilient valve member, said resilient valve member including a diaphragm portion and an outer wall portion, said diaphragm portion defining a slit therethrough and having an outer peripheral edge which generally conforms in shape to said valve member receiving cavity but is larger in dimension than said cavity when said resilient valve member is uncompressed, said outer wall portion extending away from said outer peripheral edge and generally conforming in shape to said cavity; and wherein said resilient valve member is compressively fitted within said valve member receiving cavity by advancing said outer wall portion into said cavity to thereby cause said outer peripheral edge to be compressed in dimension to fit within said cavity, with said compression collar portion of said valve housing pressing inwardly against said outer peripheral edge of said diaphragm portion to apply laterally compressive forces against said diaphragm portion and to thereby bias said slit toward a normally closed position.

* * * * *